(12) United States Patent
Camborde et al.

(10) Patent No.: US 6,511,982 B2
(45) Date of Patent: Jan. 28, 2003

(54) TREATMENT OF PAIN

(75) Inventors: Francoise Camborde, Orsay (FR); Alix Cloarec, Triel sur Seine (FR); Charles Conway, Cheshire, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 09/754,766

(22) Filed: Jan. 4, 2001

(65) Prior Publication Data

US 2001/0016584 A1 Aug. 23, 2001

Related U.S. Application Data

(63) Continuation-in-part of application No. PCT/FR00/01817, filed on Jun. 29, 2000.

(30) Foreign Application Priority Data

Jun. 30, 1999 (FR) ............................................ 99 08363

(51) Int. Cl.⁷ ............................................ A61K 31/497
(52) U.S. Cl. .................. 514/252.15; 514/922
(58) Field of Search ............................ 514/252.15, 922

(56) References Cited

U.S. PATENT DOCUMENTS

| | | |
|---|---|---|
| 4,182,763 A | 1/1980 | Casten et al. |
| 4,435,405 A | 3/1984 | Blackburn et al. |
| 4,576,953 A | 3/1986 | Le Count |
| 4,607,039 A | 8/1986 | Le Count, et al. |
| 4,794,112 A | 12/1988 | Cooper |
| 5,872,145 A | 2/1999 | Plachetka |

FOREIGN PATENT DOCUMENTS

GB   2222768   3/1990

OTHER PUBLICATIONS

Giordano, et al., "Antinociceptive effects of the novel anxiolytic buspirone in three pain tests in rats," *Pain*, 39, 1989, 109–113..
Giordano, et al., "Putative mechanisms of buspirone–induced antinociception in the rat," *Pain*, 50, 1992, 365–372.
Kishore–Kumar, et al., "Single doses of the serotonin agonists buspirone and *m*–chlorophenylpiperazine do not relieve neuropathic pain," *Pain*, 37, 1989, 223–227.
Cao, et al., "Buspirone and 1 (2–pyrimidinyl)–piperazine attenuate xylazine–induced antinociception in the mouse," *J. Pharm. Pharmacol.*, 1994, 46, 931–932.
Pascual, et al., "Buspirone in primary headaches," *Acta. Neurol. Scand.*, 1998, 97, 142.
*The Pharmacologic Basis of Therapeutics*, 5th edition, Macmillan Publishing Co., 1975, 325–358.

*Primary Examiner*—Frederick Krass
(74) *Attorney, Agent, or Firm*—Richard P. Ryan

(57) ABSTRACT

A method of treating pain with acetaminophen comprises the concurrent administration of buspirone. This combination of agents surprisingly results in a morphine-like analgesic response characterized by rapid onset, greater pain relief, and a longer duration of action.

26 Claims, 5 Drawing Sheets

TREATMENT OF PAIN

CROSS REFERENCE TO RELATED APPLICATION

This continuation-in-part application claims priority from PCT/FR00/01817 filed Jun. 29, 2000 which claims priority from French patent application 99.08363 filed Jun. 30, 1999.

BACKGROUND OF THE INVENTION

This invention relates to the use of a therapeutic combination of two compounds to treat pain. The method of pain treatment comprises co-administration of buspirone with acetaminophen (paracetamol). This combination of agents produces a more robust opioid-type analgesia providing more rapid onset and longer duration.

Acetaminophen is an established analgesic agent having only weak anti-inflammatory activity and can be classified as a non-NSAID analgesic. Ibuprofen is an example of a non-steroidal analgesic having significant anti-inflammatory properties and is classified as a non-steroidal anti-inflammatory drug (NSAID). Acetaminophen is believed to relieve pain by elevation of the pain threshold and is generally given in amounts ranging from about 600 to 1300 mg per dose in humans.

While acetaminophen is equally effective as aspirin, it is unlikely to produce many of the adverse effects of aspirin and aspirin-containing products. Acetaminophen itself, however, has been associated with a propensity for contributing to liver damage in patients that ingest significant amounts of alcohol. The dose-related toxic effect of acetaminophen on liver is demonstrated by the hepatic toxicity seen with overdosage of acetaminophen. Therefore, it would be desirable to be able to effectively treat pain utilizing lower doses of acetaminophen.

Combinations of various analgesics to provide additive effects in treating pain are known in the literature; e.g., combinations of aspirin with codeine or other narcotic analgesics are known to provide additive analgesic effects in man. See: *The Pharmacologic Basis of Therapeutics*, 5$^{th}$ edition, Macmillan Publishing Co., 1975, pp. 325–358. More active analgesic combinations are continually sought since they may be able to relieve pain with reduced dosages, thereby diminishing accompanying adverse effects and toxicities resulting from higher dosages. It is particularly desirable to discover a potentiating agent and/or a synergistic combination effect. This type of combination concerns the present invention.

Acetaminophen combinations have been previously disclosed.

Cooper, in U.S. Pat. No. 4,794,112 disclosed combinations of hydroxyzine with acetaminophen as being effective analgesic compositions.

Buspirone, chemically: 8-[4-[4-(2-pyrimidinyl)1-piperazinyl]butyl-8-azaspiro(4,5)-decane-7,9-dione, is a pharmaceutically active compound which was disclosed in U.S. Pat. No. 4,182,763 as being effective for the treatment of anxiety mixed with depression. A number of other pharmacologic actions useful in treating various clinical disorders have been reported for buspirone. Antinociceptive effects of buspirone have been described in numerous references. For example, Giordano, et al., 1989, *Pain*, 39, 109–113, suggest the potential use of buspirone in treating pain arising from chemical and mechanical nociception.

Additional study of buspirone-induced antinociception by Giordano et al., 1992, *Pain*, 50, 365–372, concluded that buspirone produced a non-opioid type of analgesia.

Roberts, et al., in GB 2,222,768 disclose and claim the use of 5-HT1-like agonists as analgesics. A group of specifically disclosed agents classified as agonists, including buspirone, were reported as being expected to exhibit analgesic activity to a greater or lesser extent than the 5-HT1 agonist 8-hydroxy-DPAT.

A study on neuropathic pain by Kishare-Kumar, et al., reported in *Pain*, 1989, 37, 223–227, indicated that acute high doses of buspirone did not relieve neuropathic pain.

Combining buspirone with other analgesic has been disclosed by B. -J. Cao, et al., in *J. Pharm. Pharmacol.*, 1994, 46, 331–332, where buspirone was demonstrated as acting to attenuate xylazine-induced antinociception. These studies were prompted by the earlier reports of buspirone's attenuation of antinociception induced by morphine and sufentanil. These reports teach away from the use of buspirone to potentiate the analgesic effect of another pain-relieving agent.

Plachetka in U.S. Pat. No. 5,872,145 discloses a method of treating migraine by the co-timely administration of a 5-HT agonist and a NSAID or non-NSAID analgesic agent. While acetaminophen is listed as an example of such a non-NSAID, buspirone is not mentioned in the patent. The intended 5-HT1 agonist prototype is sumatriptan, a member of a different 5-HT1 subclass than buspirone.

Buspirone, by itself, has been reported to be useful in the preventive treatment of headaches. Cf: Pascual, et al., *Acta. Neurol. Scand.*, 1998, 97,142.

Buspirone is commercially available from Bristol-Myers Squibb Company for the treatment of anxiety. Use in pain management is not an approved indication for buspirone.

In summary, the prior art does not disclose or suggest the novel use of buspirone to potentiate the analgesic effect of acetaminophen. The concurrent administration of buspirone with acetaminophen provides a qualitative improvement in the resulting analgesia. The onset, duration and degree of analgesia produced is morphine-like and as such is unexpected, particularly in view of reports of buspirone's attenuation of the antinociceptic effects of certain analgesics.

SUMMARY OF THE INVENTION

The present invention provides a method for treatment of pain comprising the concurrent administration of buspirone and acetaminophen in a manner which results in potentiation of the antinociceptive effects of acetaminophen. The analgesia produced by the concurrent administration of acetaminophen and buspirone is qualitatively opioid-like, resembling morphine in having a rapid onset, providing greater pain relief and maintaining the analgesic effect for a longer time. The addition of buspirone also allows for the use of smaller amounts of acetaminophen, thereby reducing the liver toxicity potential. The present invention also comprises pharmaceutical compositions and pharmaceutical kit/packaging containing acetaminophen and buspirone for combination therapy.

DETAILED DESCRIPTION OF THE INVENTION

Figure 1:
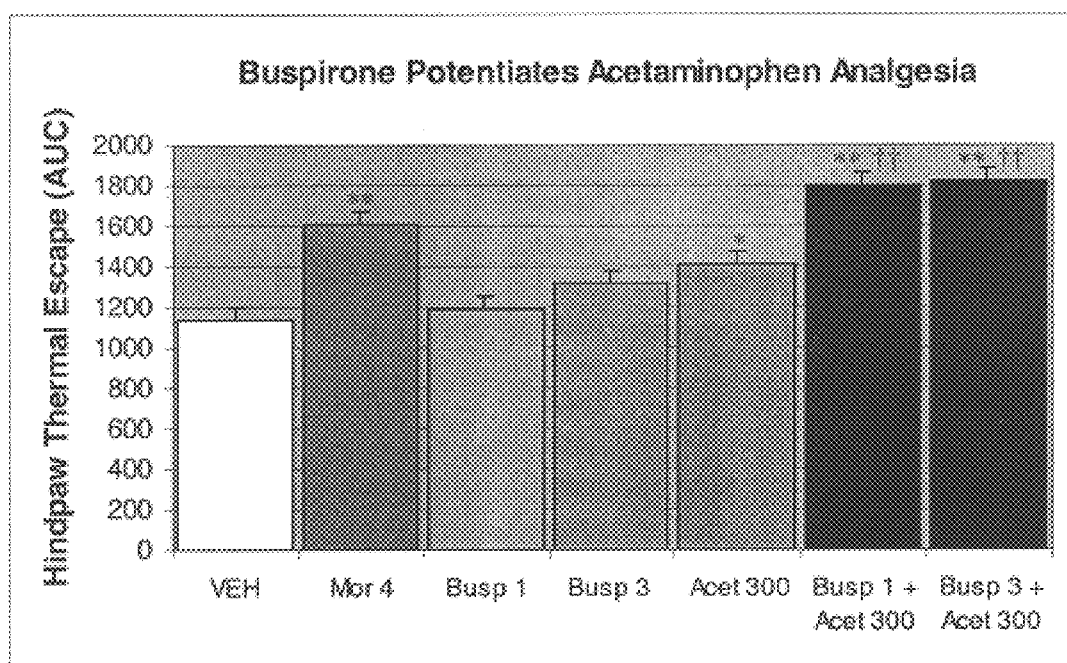
FIG. 1 Buspirone (1 or 3 mg/kg; ip) potentiates the analgesic effect of acetaminophen (300 mg/kg; ip). The hindpaw thermal escape response of albino rats was elevated significantly above vehicle (Veh) by acetamoniphen (Acet 300 mg/kg; ip). When buspirone (1 or 3 mg/kg; ip) was co-administered with acetaminophen (Busp 1+Acet 300, and Busp 3+Acet 300) the analgesic effect was greater than either compound given alone, and also exceeded that of morphine (Mor 4 mg/kg; ip). Data are expressed as mean ± sem for Area Under the Curve (AUC) as calculated from thermal escape latencies (sec) over 120 min post injection period. * p<0.05 ** p<0.01 compared to Veh, †† p<0.01 compared to single dose components.

In accordance with the present invention, pain is relieved in mammals by concurrent systemic administration of acetaminophen and buspirone or an acid salt form thereof in an amount sufficient to potentiate the analgesic activity of the acetaminophen with a total amount of acetaminophen and buspirone being an amount sufficient to relieve pain in the mammal.

The addition of buspirone to acetaminophen administration has been found to produce a marked potentiation of acetaminophen's analgesic effects. This combination therapy of buspirone with acetaminophen results in an enhanced therapeutic effect similar to morphine allowing for greater and longer-lasting efficacy with a faster onset of action. By potentiating of acetaminophen's analgesic effects, lower doses can be employed to limit the potential for adverse effects. Moreover, acetaminophen potentiated with buspirone can be used to treat severe pain for which acetaminophen alone would not be effective. Thus, this method of pain treatment widens the use of acetaminophen to treat pain of varied origins in a much larger number of patients. The present method of pain treatment is also intended for application to animals.

As used herein, the term "animal" shall refer to a vertebrate animal. More preferably, the vertebrate animal is a mammal. As used herein, the term "mammal" shall refer to the Mammalia class of higher vertebrates. The term "mammal" includes, but is not limited to, a human. The term "treating" as used herein includes prophylaxis of the named condition or amelioration or elimination of the condition and/or its characteristic symptoms once it has been established.

As used herein, the term "pain" shall refer to all types of pain. Preferably, the term shall refer to acute and chronic pains, such as neuropathic pain and post-operative pain, chronic lower back pain, cluster headaches, herpes neuralgia, phantom limb pain, central pain, dental pain, neuropathic pain, opioid-resistant pain, visceral pain, surgical pain, bone injury pain, pain during labor and delivery, pain resulting from burns, including sunburn, post partum pain, migraine, angina pain, and genitourinary tract-related pain including cystitis, the term shall also preferredly refer to nociceptive pain or nociception.

By "therapeutically effective amount" is meant an amount of acetaminophen that when administered alone is effective in providing pain relief. "Concurrent administration," "administered in combination" or similar phrases referring to the acetaminophen and buspirone components mean that the components are administered concurrently to the mammal being treated. By "concurrently," it is meant that each component may be administered at the same time or sequentially in any order at different points in time. However, if not administered at the same time, they should be administered sufficiently closely in time so as to provide the desired potentiation of treatment effect. Suitable dosing intervals and dosing order with such compounds will be readily apparent to those skilled in the art, once armed with the present disclosure. Preferably both components are administered at the same time or within an hour of each other.

The mechanism of action for buspirone is not completely understood. At present, buspirone is believed to act as an agonist at pre-synaptic 5-HT1A receptors and as a partial agonist/antagonist at post-synaptic 5-HT1A receptors. It also has agonistic action at presynaptic D2 dopaminergic receptors. Acetaminophen is believed to act by elevating the pain threshold in patients.

Acetaminophen is generally given in analgesic doses ranging from about 300 to 1300 mg and preferably from about 650 to 1300 mg with a maximum recommended daily dose of about 4000 mg. As an anxiolytic, buspirone is generally given in doses of 5 to 30 mg with recommended daily doses of about 10 to 60 mg and usually about 20 to 40 mg.

For concurrent administration in the present method of pain treatment, acetaminophen doses would be no lower than the minimally effective dose (MED) for effective analgesia. It is expected that the buspirone dose would generally be below 20 mg. There has been no clinical dose established for buspirone's use as a single agent to treat pain. Buspirone is preferably employed in acid addition salt form; e.g., the hydrochloride salt.

The precise therapeutic dose of the individual component agents, acetaminophen and buspirone, as well as the amount of a pharmaceutical combination formulation may depend on several variables. Some of these would be: route of administration, time of drug release (e.g., instant or extended), administration schedule, pain severity, condition of the patient, and the like. With respect to acetaminophen, it will be concurrently administered with the effective pain relieving potentiating amount of buspirone (or its acid salts) in a total combined pain relieving amount, in doses given 1 to 6 times a day as needed to relieve pain. In general, it is desirable to employ at least an amount of acetaminophen that by itself would be minimally effective in producing analgesia. Suitable per dose amounts for acetaminophen are from 200 to 1300 mg, but are preferably from 300 to 650 mg.

In Table 1 are shown a general and preferred dose ranges of acetaminophen, buspirone, and the weight ratio range.

TABLE 1

Acetaminophen - Buspirone Dose Ranges

|  | Acetaminophen Dose Range | Buspirone (HCl) Dose Range | Buspirone: Acetaminophen Weight Ratio Range |
|---|---|---|---|
| General: | 200–1300 | 0.5–20 | 1:10 to 1:2600 |
| Particular: | 300–650 | 1.0–10 | 1:30 to 1:650 |
| More particular: | 300–500 | 1.0–5 | 1:60–1:500 |

Consequently, the weight ratio of acetaminophen to buspirone, while selected to provide the highest level of synergy, would be generally from about 10:1 to 2600:1 and particularly about 100:1 to 1000:1.

The potentiation effect has been demonstrated in accepted rodent pain models.

In a mouse hot plate test procedure described by Eddy, et al., in *J. Pharmacol. Exp. Ther.*, 950, 98:121–137; buspirone demonstrated potentiation of acetaminophen at a buspirone to acetaminophen weight ratios of 1:3,1:10, and 1:30.

More definitive testing was done using the rat hindpaw thermal escape paradigm which is described in more detail infra. The results of these tests are displayed in FIGS. 1 to 3.

FIG. 1 demonstrates the potentiating effect of 1 and 3 mg/kg buspirone HCl on a 300 mg/kg analgesic dose of acetaminophen.

Figure 2:
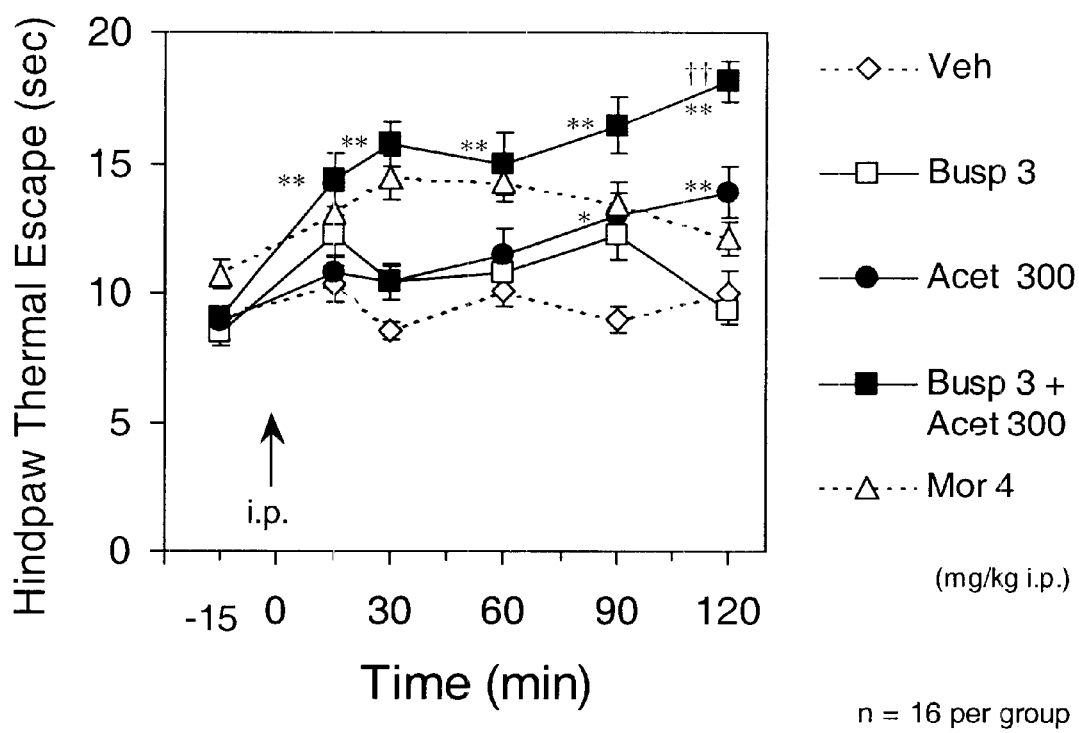
FIG. 2 Coadministration of Buspirone (3 mg/kg; ip) and Acetaminophen (300 mg/kg; ip) produces faster onset and longer lasting efficacy compared to Acetaminophen alone. The hindpaw thermal escape latency of albino rats was elevated significantly above vehicle (—◇—) at 90 and 120 min for acetaminophen (Acet 300 mg/kg; ip—●—). When buspirone (3 mg/kg; ip —□—) was co-administered with acetaminophen (Busp 3+Acet 300—■—) the analgesic onset was significantly shortened to 15 min post injection. Further, the efficacy of the combination was greater than acetaminophen alone throughout the 2 hr post-injection period, and exceeded that of morphine (Mor 4 mg/kg; ip—△—) at 90 and 120 min. Similar, though somewhat less marked, effects were observed when a lower dose (1 mg/kg) of buspirone was coadministered with acetaminophen (300 mg/kg; ip). Data are expressed as mean ± sem (n=16 rats per group). * p<0.05 ** p<0.01 compared to Veh, †† p<0.01 compared to Mor 4.

FIG. 2 shows a time course response in this model for various test agents. The 300 mg/kg dose of acetaminophen potentiated with 3 mg/kg buspirone HCl demonstrates an analgesic response superior to morphine at 4 mg/kg.

Figure 3:
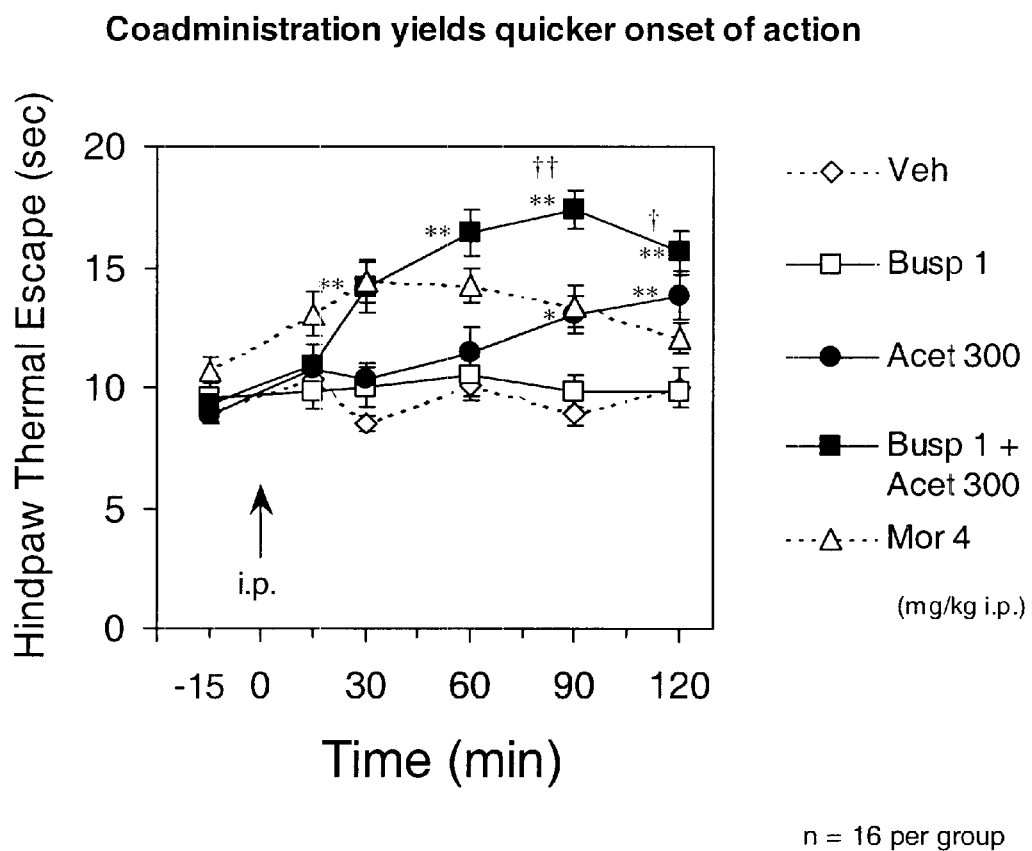
FIG. 3 Coadministration of Buspirone (1 mg/kg; ip) and Acetaminophen (300 mg/kg; ip) produces quicker onset of analgesic action as compared to Acetaminophen alone. The hindpaw thermal escape latency of albino rats was elevated significantly above vehicle (—◇—) at 90 and 120 min for acetaminophen (Acet 300 mg/kg; ip—+—). When buspirone (Busp 3 mg/kg; ip—□—) was co-administered with acetaminophen (Busp 3+Acet 300—■—) the analgesic onset was significantly shortened to 30 min post injection giving a more morphine-like response(—△—). Data are expressed as mean ± sem (n=16 rats per group). * p<0.05 ** p<0.01 compared to Veh, † p<0.05 †† p<0.01 compared to Mor 4.
Figure 4:
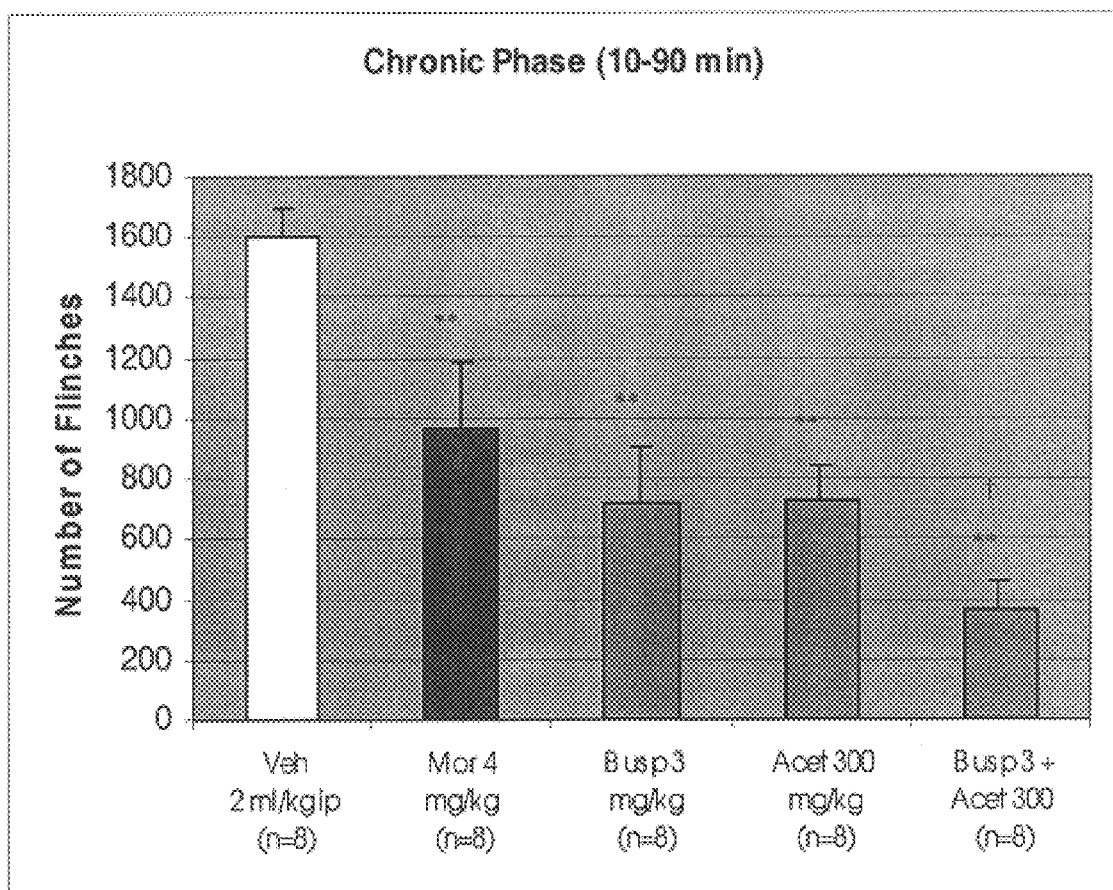
FIG. 4. Coadministration of Buspirone (3 mg/kg) and Acetaminophen (300 mg/kg) produces potent analgesia against chronic pain that is superior to Morphine (4 mg/kg). The formalin-induced flinches of albino rats was significantly suppressed, relative to vehicle (Veh 2 ml/kg ip), by single intraperitoneal delivery of morphine (4 mg/kg), buspirone (Busp 3 mg/kg), or acetaminophen (Acet 300 mg/kg). When buspirone and acetaminophen were coadministered (Busp 3+Acet 300), a even greater suppression of the chronic pain response was observed which was significantly superior to morphine. Data are expressed as mean ± sem (n=8 rats per group). ** p<0.01 compared to Veh, † p<0.05 compared to Mor 4.
Figure 5:
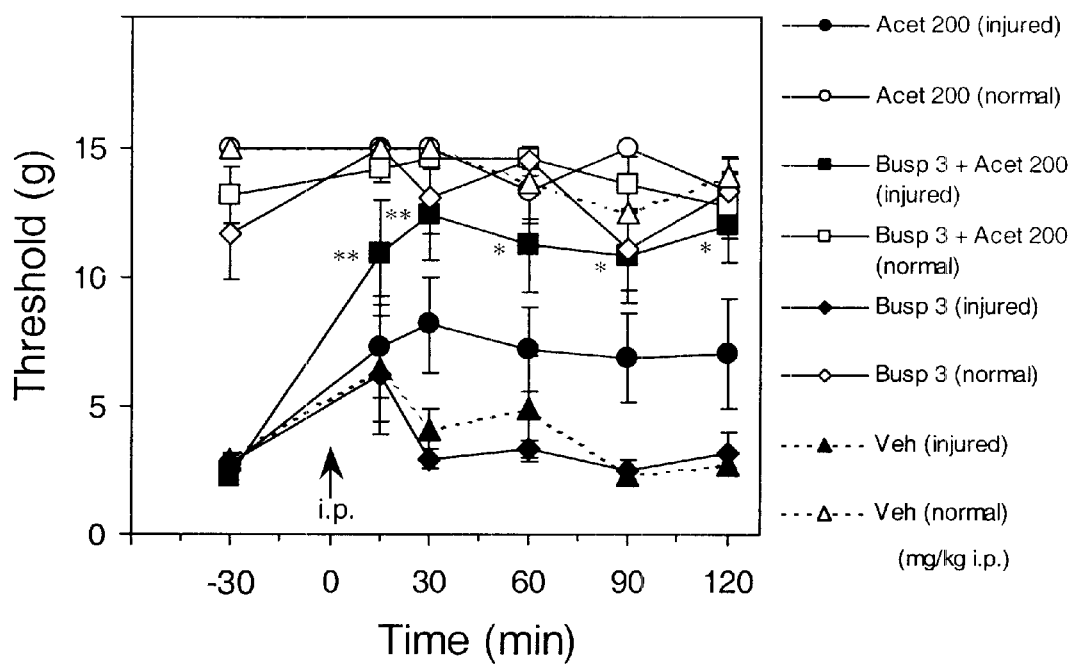
FIG. 5. Coadministration of Buspirone (3 mg/kg) and Acetaminophen (200 mg/kg) produces a rapid (15 min) onset, complete reversal of rat neuropathic pain responses. Following unilateral spinal nerve (L5/L6) ligation (Chung model), vehicle (2 ml/kg ip) treated animals exhibit hypersensitive responses to light touch with a von Frey hair on the injured side (Veh (injured)), but not the non-operated side (Veh (normal)) during baseline testing (−30 min). Following drug delivery (at 0 min), none of the compounds produced significant differences in the von Frey thresholds for the normal side (see open symbols) as compared to vehicle (Veh (normal)) at any of the post-injection test times (15, 30, 60, 90 or 120 min). Likewise, for the injured side (filled symbols), treatment with buspirone (3 mg/kg ip; Busp 3 (injured)) was not significantly different from vehicle (Veh (injured)). Although acetaminophen (200 mg/kg ip; Acet 200 (injured)) produced a partial reversal toward normal at 30–120 min, significant differences persisted between the injured (Acet 200 (injured)) and normal (Acet 200 (normal)) sides throughout the study. In contrast, following coadministration of buspirone and acetaminophen (Busp 3+Acet 200), there was a complete reversal of the neuropathic pain responses on the injured side (Busp 3+Acet 200 (injured)), such that differences between the injured and normal side were no longer present. Importantly, this was a rapid onset (beginning at 15 min), long lasting effect (persisted at least 120 min). Data are expressed as mean ± sem (n=8 rats per group). ** p<0.01 * p<0.05 compared baseline (−30).

Potentiating a 300 mg/kg dose of acetaminophen with 1 mg/kg buspirone HCl yields a faster onset of action as shown in FIG. 3.

These data, taken together, demonstrate that the concurrent administration of a potentiating amount of buspirone with a minimally effective acetaminophen dose results in analgesia which is faster in onset, more efficacious and has a longer duration of action.

With regard to single agent or combined agent formulations of acetaminophen and buspirone to be employed in the present method, considerable variation in formulations and components may be practiced without departing from the present invention. Any salt form of buspirone having acceptable formulation properties can be used. However, the HCl salt form is preferred.

The present invention then comprises the concurrent administration of a therapeutically effective amount of acetaminophen and an analgesia-potentiating amount of buspirone or one of its acceptable salts or hydrates.

The present invention also includes pharmaceutical combination compositions comprising the buspirone and acetaminophen components. Such compositions may be in solid or liquid dosage units and may further include suitable pharmaceutical carriers and excipients.

The compositions of this invention may be suitable for administration to an animal. Such animals include both domestic animals; for example, livestock, laboratory animals and household pets, and non-domestic animals such as wildlife. More preferably, the animal is a vertebrate. Most preferably, a compound of this invention shall be administered to a mammal. It is especially preferred that the animal is a domestic mammal or a human. For such purposes, a compound of this invention may be administered as a feed additive.

The most preferred mammal is a human.

Pharmaceutical kit packaging is also envisioned for the present invention. In the kit package are provided both acetaminophen and buspirone unit dosage forms for use in the present method.

Dosage and Formulation

The buspirone component and acetaminophen component combination treatment of the invention can be given via parenteral, rectal, buccal, transdermal, or, preferably, oral routes of administration by any conventional means available for the use in conjunction with pharmaceuticals, either as individual separate dosage units administered simultaneously or concurrently, or in a physical combination of each component therapeutic agent in a single or combined dosage unit. The active agents can be administered alone, but are generally administered with a pharmaceutical carrier selected on the basis of standard pharmaceutical practice.

In general, acetaminophen would be administered at levels in accordance with guidelines found in standard medical/ drug references such as the *Physicians Desk Reference* and the like. This would be in the range of about 300 to 1300 mg per dose. Amounts of buspirone for concurrent administration would be in the range of from about 0.5 to 20 mg and preferably from 1 to 5 mg per dose.

The dosage administered will, of course, vary depending on the use and known factors such as the age, health, and weight of the recipient; nature and extent of symptoms, concurrent treatments, if any, frequency of treatment, and the effect desired. The recipient may be any type of mammal, but is preferably a human.

In the methods of the present invention, the two compounds, buspirone and acetaminophen form the active ingredients, and are typically administered in admixture with suitable pharmaceutical diluents, excipients, or carriers (collectively referred to herein as carrier materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, and the like. Disintegrators include, without limitation, starch, methyl cellulose, agar, bentonite, xanthan gum, and the like.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

The combination products of this invention may be formulated such that, although the active ingredients are combined in a single dosage unit, the physical contact between the active ingredients is minimized. In order to minimize contact, for example, one or more of the active ingredients may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. Another embodiment of this invention provides for a combination product wherein one or more of the active ingredients is coated with a sustained-release material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one or more components is coated with a sustained and/or enteric release polymer, and the other(s) component is also coated with a polymar such as a low viscosity grade of hydroxypropyl methylcellulose or other appropriate materials as known in the art, in order to further separate the active components. The polymer coating serves to form an additional barrier to interaction with the other component.

Dosage forms of the combination products of the present invention wherein one active ingredient is enteric coated can be in the form of tablets such that the enteric coated component and the other active ingredients are blended together and then compressed into a tablet or such that the enteric coated component is compressed into one tablet layer and the other active ingredient is compressed into an additional layer. Optionally, in order to further separate the two layers, one or more placebo layers may be present such that the placebo layer is between the layers of active ingredients. In addition, dosage forms of the present invention can be in the form of capsules wherein one active ingredient is compressed into a tablet or in the form of a plurality of microtablets, particles, granules or non-perils, which are then enteric coated. These enteric coated microtablets, particles, granules or non-perils are then placed into a capsule or compressed into a capsule along with a granulation of the other active ingredient.

These as well as other ways of minimizing contact between the components of combination products of the present invention, whether administered in a single dosage form or administered in separate forms but at the same time or concurrently by the same manner, will be readily apparent to those skilled in the art, based on the present disclosure.

Specific Embodiments

Pharmaceutical kits or packaging containing separate unit dosage forms of buspirone and acetaminophen are another aspect of the present invention. Acetaminophen and buspirone dosage forms constituting the combination are packed separately but packaged together as in kit form. Preferably the buspirone and acetaminophen formulations are suited for the same route of administration and are intended to be given concurrently.

Most preferably, the solid oral formulations are contained in packaging materials which protect the formulations from moisture and light. For example, suitable packaging materials include amber colored high density polyethylene bottles, amber colored glass bottles, and other containers made of a material which inhibits the passage of light. Most preferably, the packaging will include a desiccant pack. The container may be sealed with an aluminum foil blister to provide the desired protection and maintain product stability.

All the above-mentioned embodiments of concurrent administration of the acetaminophen and buspirone components are intended for use as an improved method of treating pain. For example, their use is suited for the treatment of articular pain, and in particular in the treatment of arthritis, rheumatoid arthritis, spondylitis, gouty arthritis, osteoarthritis, and juvenile arthritis.

These embodiments can also be used within the context of the treatment of dysmenorrhea, tendinitis, and bursitis. They can also be used in the treatment of pain symptoms of myalgia, dental pain, and migraine, in the treatment of pain of cancerous origin, and also as additional treatments for infectious and febrile states.

Finally, these embodiments can find use in the treatment of neuropathic pain, and in particular of nervous pain, herpes zoster, desafferentation (phantom member) pain, diabetic neuropathies.

Examples of acetaminophen-buspirone combination pharmaceutical formulations are given below. These examples are intended to be instructive but not exhaustive. Those skilled in the pharmaceutical arts will readily envision alternate formulations applicable to the combination embodiment of the present invention.

The preparation of buspirone can be found in the literature; e.g., see U.S. Pat. No. 3,717,634. Other synthetic processes for buspirone have been disclosed and both buspirone and acetaminophen are available commercially from bulk drug manufacturers.

Acetaminophen and buspirone combinations of the present invention may be formulated according to the following non-limiting examples.

EXAMPLE 1

| Gelatine capsule (Size No. 1) | |
|---|---|
| Acetaminophen | 500 mg |
| Buspirone HCl | 2.5 mg |
| Microcrystalline cellulose | 100 mg |
| Hydroxypropyl methyl cellulose | 10 mg for one gelatine capsule |

EXAMPLE 2

| Tablet | | |
|---|---|---|
| Acetaminophen | 500 mg | |
| Buspirone HCl | 5 mg | |
| Microcrystalline cellulose | 100 mg | |
| Lactose | 100 mg | |
| Hydroxypropyl methyl cellulose | 10 mg | |
| Magnesium stearate | 5 mg | |
| Hydroxypropyl cellulose | 50 mg | for one tablet |

EXAMPLE 3

| Injectable preparation | |
|---|---|
| Acetaminophen | 1000 mg |
| Buspirone HCl | 10 mg |
| Cysteine | 50 mg |
| PEG 400 | 30 mg |
| Ethyl alcohol | 10 mg |
| Water preparation for injection | q.s.p. 100 ml |

Various modifications of the invention in addition to those shown and described herein will be apparent to those skilled in the art in view of the foregoing description. Such modifications are within the scope of the following claims.

EXAMPLE 4

| Suppository | | |
|---|---|---|
| Acetaminophen | 1000 mg | |
| Buspirone HCl | 20 mg | |
| Semi-synthetic glyceride | 2000 mg | for one suppository |

Transdermal delivery vehicles for buspirone may be suitably adapted for use in the present invention. See WO 97/37659.

Experimental Procedure for Rat Hindpaw Withdrawal Test for Analgesia (Acute Pain)

To assess the thermally evoked paw-withdrawal response, a commercially available device was used. Specifics of device construction and operation have been published previously (Dirig D M, Salami A, Rathbun M L, Ozaki G T, Yaksh T L. Characterization of variables defining hindpaw withdrawal latency evoked by radiant thermal stimuli. J Neurosci Methods. Oct. 3, 1997; 76(2):183–91). This device is comprised of a glass surface on which the rats were placed individually in Plexiglas cubicles (9×22×25 cm). The surface is maintained at 30° C. by a feedback-controlled, under-glass, forced-air heating system. The thermal nociceptive stimulus originates from a projection bulb below the glass that can be manipulated in a two-dimensional axis on ball bearing slides. This apparatus allows the stimulus to be delivered separately to each hind paw with the aid of an angled mirror mounted on the stimulus source. A timer is actuated with the light source, and escape latency is defined as the time between stimulus onset and the display of a brisk paw withdrawal (detected by photodiode motion sensors that stopps the timer and terminates the stimulus; cut-off time for a non-response is 20 sec which triggers automatic termination of the stimulus). In the present study, animals are placed in test boxes for 30 min acclimation and then baseline escape latency is assessed separately for each hindpaw (left and right) at −15 min. All drugs are delivered at 0 min by the intraperitoneal (i.p.) route in a volume of 3 ml/kg. The vehicle for buspirone-HCl (MJ-009022) and morphine sulfate (Sigma, M8777) was 0.9% sodium chloride (Saline). For acetaminophen (Sigma, A7085) the vehicle was 40% polyethylene glycol 400 (PEG-400), 10% EtOH, 15% Tween 80, and 35% deionized H2O (PETW). Acetaminophen was disolved sequentially in two parts: 1) first into a solution of 80% PEG 400+20% EtOH, and 2) then slowly added to it was an equal volume of 30% Tween 80+70% deionized H2O (sonicated as needed). Each animal received two injections at time zero.

Specifically, animals were tested in one of the following 10 treatment conditions (abbreviations used in figures are shown under 'Key" below):

| Cond | Key | Dual Injection (each injected separately; 3 ml/kg; ip) |
|---|---|---|
| a) | Veh | Vehicle + Vehicle (Saline + PETW) |
| b) | Mor 4 | morphine (4 mg/kg) + Saline |
| c) | Busp 1 | buspirone (1 mg/kg) + PETW |
| d) | Busp 3 | buspirone (3 mg/kg) + PETW |
| e) | Acet 100 | acetaminophen (100 mg/kg) + Saline |
| f) | Acet 300 | acetaminophen (300 mg/kg) + Saline |
| g) | 1 + 100 | buspirone (1 mg/kg) + acetaminophen (100 mg/kg) |
| h) | 3 + 100 | buspirone (3 mg/kg) + acetaminophen (100 mg/kg) |
| i) | 1 + 300 | buspirone (1 mg/kg) + acetaminophen (300 mg/kg) |
| j) | 3 + 300 | buspirone (3 mg/kg) + acetaminophen (300 mg/kg) |

Following drug administration, thermal escape latencies are measured at 15, 30, 60, 90 and 120 min (mean of both paws is used for statistical analysis).

Preclinical Model of Chronic Pain (Rat Formalin Test)

To assess responses to a chronic stimulus (subcutaneous formalin injection), animals are first placed in clear observation boxes for a 30 min acclimation period prior to testing. Animals are subsequently removed and the dorsum of one hindpaw is injected s.c. with 50 microliters of 2.5% formalin. Animals exhibit a repetitive flicking of the injected paw called 'flinches'. The total number of flinches is computer scored during the chronic phase (10–90 min after formalin) using a commercially available device (George Ozaki, Automated Nocicpetion Analyzer, Department of Anesthesiology, University of California, San Diego; La Jolla, Calif.) which automates the manual procedure described previously by Wheeler-Aceto et al. (Pain 40:229–238, 1990). All drugs are delivered at 30 min prior to formalin injection by the intraperitoneal (i.p.) route in a volume of 2 ml/kg. The vehicle for buspirone-HCl (MJ-009022) and morphine sulfate (Sigma, M8777) was 0.9% sodium chloride (Saline). For acetaminophen (Sigma, A7085) the vehicle was 40% polyethylene glycol 400 (PEG-400), 10% EtOH, 15% Tween 80, and 35% deionized H2O (PETW). Acetaminophen was disolved sequentially in two parts: 1) first into a solution of 80% PEG 400+20% EtOH, and 2) then slowly added to it was an equal volume of 30% Tween 80+70% deionized H2O (sonicated as needed). Each animal received two injections at time zero. Specifically, animals were tested in one of the following 5 treatment conditions (abbreviations used in figures are shown under 'Key" below):

| Cond | Key | Dual Injection (each injected separately; 3 ml/kg; ip) |
|---|---|---|
| a) | Veh | Vehicle + Vehicle (Saline + PETW) |
| b) | Mor 4 | morphine (4 mg/kg) + Saline |
| c) | Busp 3 | buspirone (3 mg/kg) + PETW |
| d) | Acet 300 | acetaminophen (300 mg/kg) + Saline |
| e) | 3 + 300 | buspirone (3 mg/kg) + acetaminophen (300 mg/kg) |

Preclinical Model of Neuropathic Pain (Chung Surgery & Von Frey Test)

To test agents for activity against nerve injury-induced tactile allodynia, animals were surgically prepared with unilateral tight ligation of spinal nerves L5 and L6 following the method of Kim and Chung (1992). See Kim S H, Chung J M. An experimental model for peripheral neuropathy produced by segmental spinal nerve ligation in the rat. Pain. 1992; September 50(3): 355–63. After 1–4 weeks recovery, paw withdrawal to light touch was assessed as described by Chaplan et al.(1994). See Chaplan S R, Bach F W, Pogrel J W, Chung J M, Yaksh T L. Quantitative assessment of tactile allodynia in the rat paw. J Neurosci Methods. 1994 July; 53(1): 55–63. In brief, rats are placed in a plastic cage with a wire mesh bottom and allowed to acclimate for 30 minutes, until cage exploration and grooming stops. The plantar surface of each hind paw is touched with 1 of a series of von Frey hairs with varying stiffness requiring a known force to buckle. A positive response is noted if the paw is sharply withdrawn. In the present study, after acclimation the baseline von Frey thresholds are assessed for each hindpaw (one normal, one injured) at −30 min. All drugs are delivered at 0 min by the intraperitoneal (i.p.) route in a volume of 2 ml/kg. The vehicle for buspirone-HCl (MJ-009022) and morphine sulfate (Sigma, M8777) was 0.9% sodium chloride (Saline). For acetaminophen (Sigma, A7085) the vehicle was 40% polyethylene glycol 400 (PEG-400), 10% EtOH, 15% Tween 80, and 35% deionized H2O (PETW). Acetaminophen was disolved sequentially in two parts: 1) first into a solution of 80% PEG 400+20% EtOH, and 2) then slowly added to it was an equal volume of 30% Tween 80+70% deionized H2O (sonicated as needed). Each animal received two injections at time zero. Specifically, animals were tested in one of the following 4 treatment conditions (abbreviations used in figures are shown under 'Key" below):

| Cond | Key | Dual Injection (each injected separately; 2 ml/kg; ip) |
|---|---|---|
| a) | Veh | Vehicle + Vehicle (Saline + PETW) |
| b) | Busp 3 | buspirone (3 mg/kg) + PETW |
| c) | Acet 200 | acetaminophen (200 mg/kg) + Saline |
| d) | 3 + 200 | buspirone (3 mg/kg) + acetaminophen (200 mg/kg) |

Following drug administration, von Frey thresholds are measured at 15, 30, 60, 90 and 120 min.

What is claimed is:

1. A method for the treatment of pain by the concurrent administration of acetaminophen and a pain-relieving potentiating amount of buspirone or a pharmaceutically acceptable salt or solvate thereof.

2. The method of claim 1 wherein buspirone HCl is the pharmaceutically acceptable salt of buspirone.

3. The method of claim 1 wherein acetaminophen and buspirone are administered separately.

4. The method of claim 1 wherein acetaminophen and buspirone are administered in combination.

5. The method of claim 1 wherein at least 200 to 1300 mg of acetaminophen and at least 0.5 to 20 mg of buspirone or an acid salt form thereof are administered.

6. A pharmaceutical composition comprising a therapeutically effective amount of acetaminophen and a pain-relieving potentiating amount of buspirone or a pharmaceutically acceptable salt thereof.

7. The composition of claim 6 in which the weight ratio of buspirone to acetaminophen is from 1:10 to 1:2600.

8. The composition of claim 6 in which the weight ratio of buspirone to acetaminophen is from 1:30 to 1:650.

9. The composition of claim 6 in which the weight ratio of buspirone to acetaminophen is from 1:60 to 1:500.

10. The pharmaceutical composition of claim 6 wherein the pharmaceutically acceptable salt of buspirone is buspirone HCl.

11. The pharmaceutical composition of claim 6 in unit dose form.

12. The pharmaceutical composition of claim 7 in unit dose form.

13. The pharmaceutical composition of claim 8 in unit dose form.

14. The pharmaceutical composition of claim 9 in unit dose form.

15. A pharmaceutical kit package containing therapeutically effective dosage forms of acetaminophen and effective potentiating dosage forms of buspirone.

16. The pharmaceutical composition of claim 6 in a formulation suitable for oral administration.

17. The pharmaceutical composition of claim 7 in a formulation suitable for oral administration.

18. The pharmaceutical composition of claim 8 in a formulation suitable for oral administration.

19. The pharmaceutical composition of claim 9 in a formulation suitable for oral administration.

20. The pharmaceutical composition of claim 6 in a formulation suitable for parenteral administration.

21. The pharmaceutical composition of claim 6 in a formulation suitable for transdermal administration.

22. The pharmaceutical composition of claim 6 in a formulation suitable for buccal administration.

23. The pharmaceutical composition of claim 6 in a formulation suitable for rectal administration.

24. The method of claim 1 wherein said pain is chronic pain.

25. The method of claim 1 wherein said pain is acute pain.

26. The method of claim 1 wherein said pain is neuropathic pain.

* * * * *